(12) United States Patent
Tüttemann et al.

(10) Patent No.: US 11,857,446 B2
(45) Date of Patent: Jan. 2, 2024

(54) ORTHOPEDIC DEVICE

(71) Applicant: Ottobock SE & Co. KGaA, Duderstadt (DE)

(72) Inventors: Markus Tüttemann, Waltrop (DE); Carsten Vogel, Duderstadt (DE); Oliver Mizera, Göttingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 233 days.

(21) Appl. No.: 17/095,222

(22) Filed: Nov. 11, 2020

(65) Prior Publication Data

US 2021/0137717 A1    May 13, 2021

(30) Foreign Application Priority Data

Nov. 11, 2019   (DE) ...................... 10 2019 130 391.5

(51) Int. Cl.
*A61F 5/01*   (2006.01)

(52) U.S. Cl.
CPC ...... *A61F 5/0102* (2013.01); *A61F 2005/016* (2013.01); *A61F 2005/0158* (2013.01); *A61F 2005/0165* (2013.01)

(58) Field of Classification Search
CPC ...... A61F 2005/0132; A61F 2005/0134; A61F 2005/0137; A61F 2005/0141; A61F 2005/0146; A61F 2005/0148; A61F 2005/0155; A61F 2005/0158; A61F 2005/016; A61F 2005/0165;
(Continued)

(56) References Cited

U.S. PATENT DOCUMENTS

| | | | | |
|---|---|---|---|---|
| 4,433,679 A | * | 2/1984 | Mauldin | ............... A61F 5/0102 602/26 |
| 2005/0187506 A1 | * | 8/2005 | Reinhardt | ............. A61F 5/0125 602/30 |

(Continued)

FOREIGN PATENT DOCUMENTS

| | | | | |
|---|---|---|---|---|
| DE | 102014114430 A1 | * | 2/2016 | ........... A61F 5/0102 |
| DE | 10 2018 217 497 A1 | | 4/2020 | |
| DE | 10 2019 119 645 A1 | | 1/2021 | |

*Primary Examiner* — Ophelia A Hawthorne
*Assistant Examiner* — Michael Milo
(74) *Attorney, Agent, or Firm* — WCF IP

(57) ABSTRACT

Examples include an upper joint arm for engaging a wearer's upper torso, connected to a first positive-locking element, and include a lower joint arm for engaging the wearer's upper leg body, and have a force application lever with a second positive-locking element, and a a mechanical energy store between the force application lever and the second joint arm. The first and second positive-locking element are aligned on a common axis, and are axially movable for engagement and disengagement. A safety device provides, in a mechanical engaging of the first and second positive-locking element, a corrective rotating of one or both the positive-locking elements. This rotation adjusts initial misalignments of the first positive-locking element and the second positive-locking element. The first positive-locking element and second positive-locking element, when engaged, transfer swivelling of the first joint arm relative to the second joint arm into a charging-discharging of the mechanical energy store.

9 Claims, 8 Drawing Sheets

(58) Field of Classification Search
CPC ............ A61F 2005/0167; A61F 5/0102; A61F
5/0123; A61F 5/0125; A61F 5/0193;
A61F 5/022; A61F 2/64; A61F 2/646;
A61H 1/0266; A61H 1/0274; A61H
1/0277; A61H 1/0281; A61H 1/0285;
A61H 1/0288; A61H 1/0292; A61H
1/0296
USPC .......... 602/5, 16, 20, 23, 26, 27, 28, 29, 32;
601/33, 34, 35
See application file for complete search history.

(56) References Cited

U.S. PATENT DOCUMENTS

| | | |
|---|---|---|
| 2015/0190249 A1* | 7/2015 | Ishibashi .................. A61F 5/01 623/24 |
| 2017/0196712 A1 | 7/2017 | Kazerooni et al. |
| 2017/0360588 A1 | 12/2017 | Yangyuenthanasan et al. |

* cited by examiner

ORTHOPEDIC DEVICE

BACKGROUND

Orthopedic devices for supporting a lower back of a user have been known from the prior art for many years. One example of this type of device is described in DE 10 2019 119 645, which has not been pre-published. Such devices are used especially for lifting in order to provide support to the person who is to lift, for instance, a heavy object. Moreover, such devices are used for persons who have to work in a bent position.

Another of this type of device is described, for instance, in US 443,113 ("the '113 reference"). The '113 device It features upper leg elements that are arranged on the upper legs of the wearer. The '113 device is also arranged on the upper body of the wearer via shoulder straps.

The '113 device includes leaf spring elements that are situated between the shoulder straps and the upper leg elements, in an arrangement such that the leaf spring elements are bent when bending down and thereby charged with potential energy. This causes the leaf spring elements to exert a force on the upper body and that force supports the extension of the body.

However, in the '113 device's arrangement, the resulting force is always exerted when an angle between the upper body and the upper legs changes. For example, the force is exerted when climbing stairs or sitting, which is at the very least uncomfortable, but possibly even disruptive and uncomfortable.

Devices that work on a similar principle are known, for example, from US 201 7/01 9671 2 A1 and US 2017/0360588 A1. However, the force that supports the lower back or the upper body, which should make it easier for the person to straighten up, is not always exerted. In the formerly named prior art, the force is only exerted when a certain angle of inclination, i.e. when the angle between the upper body element of the device and the upper leg element of the device is smaller than a predetermined angle, is exceeded. Up until this angle, the upper body can be inclined relative to the upper leg without charging an actuator or energy store. Nevertheless, in the case of this device, a supporting force always acts when the upper body assumes an angle relative to the upper leg that is smaller than a predetermined limit angle, i.e. the upper body is inclined relative to the upper leg.

The latterly named prior art comprises a device with which the supporting force is always exerted when the upper body assumes a predetermined angle relative to the vertical, i.e. in the direction along which the weight force acts. This prevents the force from acting, for instance, when the wearer of the device sits, provided that the upper body does not exceed the predetermined angle to the vertical. However, if the person leans so far when sitting that the predetermined angle is exceeded, a supporting force is automatically exceeded.

The disadvantage of all the above-named options is that secure adjustment is not possible and it cannot be ensured that the force is only exerted when it is needed and wanted; rather, situations and movements may also occur that do not require a supporting force or the lower back need not be strained or supported. This problem has been rectified by way of the device specified in DE 10 2019 119 645.

The problem was solved in that the mechanical energy store can be charged and discharged when the two gearwheels are engaged with one another. This happens when a certain criteria has been fulfilled. In the example of an embodiment specified, the two gearwheels are brought into engagement with each other when the upper body of the wearer of the device exceeds a certain angle in relation to the pelvic area. The disadvantage, however, is that up to this point the two gearwheels can move relative to each other, so that it is not clear in advance how the teeth of the gearwheels are oriented towards each other when the gearwheels are to be engaged. It can therefore happen that the teeth only engage with each other in a very small area, namely the tips of the teeth. This is not a secure positive-fit, especially with larger forces to be transmitted, so that there is a risk that the two gearwheels slip off each other and energy stored in the mechanical energy store is released in an uncontrolled manner.

The invention therefore aims to further develop an orthopedic device of the type mentioned above in such a way that this problem is eliminated or at least alleviated.

SUMMARY

The invention solves the problem by way of an orthopedic device according to the generic term in claim 1, characterized in that it has a safety device which ensures that, irrespective of the position of the first positive-locking element and the second positive-locking element relative to one another, the two positive-locking elements can be engaged with one another in such a way that a force exerted by the charged mechanical energy store is transmitted from the second positive-locking element to the first positive-locking element. This ensures that the uncontrolled release of energy when the positive-locking elements slip against each other is prevented.

The positive-locking elements feature recesses and/or projections that are designed in such a way that the two positive-locking elements can be positively engaged with one another. They are preferably gearwheels, particularly spur gearwheels.

In principle, different mechanisms with which the safety device solves the posed problem are conceivable. The safety device is preferably configured to rotate the positive-locking elements relative to one another when or after the two positive-locking elements are engaged with one another. If, at the point at which they should be engaged with one another, the positive-locking elements have positioned themselves in relation to one another in such a way that the projections and/or recesses of the two positive-locking elements can only be brought into engagement with each other in a small region rather than fully, the rotation of the two positive-locking elements relative to one another can change this relative position, thereby ensuring complete or at least greater engagement.

The invention relates to an orthopedic device which comprises a joint with a first joint element, which has a first joint arm with a first positive-locking element, and a second joint element that can be swivelled relative to the first joint element, said second joint element comprising a second joint arm and a force application lever with a second positive-locking element and a mechanical energy store, which is arranged between the force application lever and the second joint arm, wherein the mechanical energy store can be charged and discharged by swivelling the first joint arm relative to the second joint arm when the first positive-locking element is engaged with the second positive-locking element.

BRIEF DESCRIPTION OF THE DRAWINGS

In the following, some examples of embodiments of the present invention will be explained in more detail by way of the attached figures: They show

DETAILED DESCRIPTION

Figure 1:
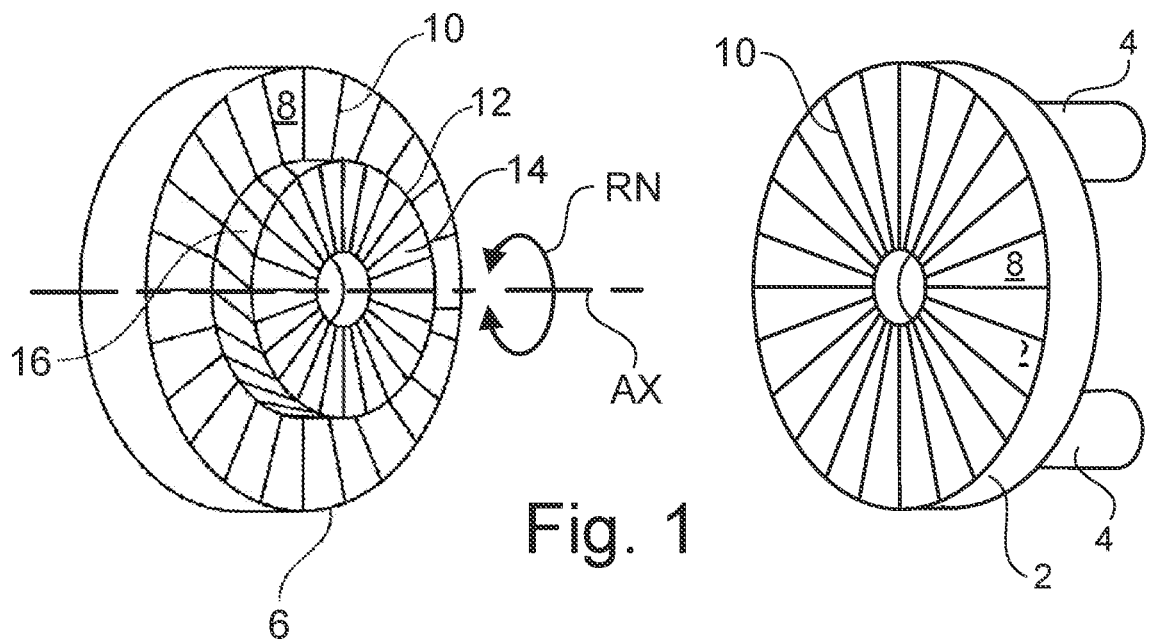
FIG. 1 is a schematic representation of positive-locking element structure in a safety device according to a first example of an embodiment of the present invention, FIG. 2 —schematically depicts one of various forms of teeth that can be used in the example embodiment shown in FIG. 1, and FIG. 3 —schematically depicts another configuration, showing an example first gearwheel with central bore with a grooved or toothed inner wall.

According to various embodiments the first positive-locking element and the second positive-locking element preferably feature frontal projections and/or recesses. This is the case, for instance, with spur gearwheels. A spur gearwheel is understood to mean a gearwheel whose teeth protrude in the axial direction. The teeth of conventional gearwheels are arranged on the outer circumference of the gearwheel and protrude in the radial direction. The spur gearwheel, like a conventional gearwheel has a rotational axis, about which the gearwheel is rotatably mounted and in relation to which the terms axial and radial are to be understood. The teeth of a spur gearwheel, however, are situated on a front surface of the gearwheel and therefore protrude in the axial direction. If two such spur gearwheels are engaged with one another, all the teeth of one gearwheel preferably engage with the teeth of the other gearwheel, resulting in a considerably larger contact area than with conventional gearwheels, whose teeth are arranged on the external circumference. This allows a greater force to be transmitted.

In accordance with disclosed embodiments, when #two such spur gearwheels whose teeth are not optimally positioned in relation to one another are being engaged with one another, this positioning can be corrected by rotating the two gearwheels relative to each other. In this case, the required rotation is preferably small, specifically smaller than 5°, preferably smaller than 3°, especially preferably smaller than 2°. This also applies to positive-locking elements that are not gearwheels with teeth, but which feature other recesses and/or projections.

It is especially preferable if the safety device features a guide spindle that protrudes axially from one of the positive-locking elements and which has frontal recesses and/or projections, specifically spur gearing that is configured to engage with the respective other positive-locking element.

It is advantageous if the guide spindle can be displaced in the axial direction relative to the positive-locking element from which it protrudes axially, the guide spindle being designed in such a way that, upon axial displacement, the guide spindle is rotated about its longitudinal axis such that a torque is applied to the positive-locking element that engages with the frontal projections and/or recesses of the guide spindle. In such a configuration, the guide spindle protrudes axially from the front surface of one of the two positive-locking elements when the two positive-locking elements are not engaged with one another. If the two positive-locking elements are now to be brought into engagement with one another, one of the two positive-locking elements—preferably the one with no guide spindle protruding from it—moves towards the respective other positive-locking element. The frontal projections and/or recesses, in particular the spur gearing of the guide spindle, first come into contact with the frontal recesses and/or projections of the other positive-locking element. However, this does not stop the movement of the other positive-locking element towards the positive-locking element with the guide spindle: rather, the guide spindle is displaced in the axial direction and moved into the positive-locking element on which it is arranged.

Preferably the frontal projections and/or recesses, in particular the spur gearing of the guide spindle with the frontal recesses and/or projections, in particular with the spur gearing of its positive-locking element, form a continuous toothing when the guide spindle is axially displaced into its gear wheel to such extent that a single continuous front surface is formed.

If the projections and/or recesses of the other positive-locking element, which has been displaced towards the guide spindle, do not engage optimally in its projections and/or recesses, the guide spindle exerts a torque on this positive-locking element, thereby rotating it into the optimal position for engaging in the recesses and/or projections of the other positive-locking element. This optimal position is reached when the guide spindle is completely recessed in its positive-locking element. This ensures that the projections and/or recesses of the two positive-locking elements engage with one another in the optimal position relative to one another, irrespective of the position of the two positive-locking elements relative to one another when they are to be brought into engagement.

Alternatively or additionally, the first positive-locking element and/or the second positive-locking element has two partial positive-locking elements, such as two partial gearwheels, which can be moved independently of each other in the axial direction. If the two positive-locking elements in this configuration are moved towards one another in order to engage them, one of the partial positive-locking elements of a positive-locking element engages in the projections and/or recesses of the other positive-locking element before the remaining partial positive-locking elements do the same. The partial positive-locking elements are preferably arranged at an offset to each other in the circumferential direction, so that the projections and/or recesses, particularly teeth of each of the partial positive-locking elements, are arranged equidistant from one another, but there is an angular offset between the projections and/or recesses, particularly between teeth of adjacent partial positive-locking elements. This ensures that the projections and/or recesses of different partial positive-locking elements engage with the projections and/or recesses of the other positive-locking element to varying degrees when the two positive-locking elements are brought into engagement with one another.

Therefore, if the projections and/or recesses of the first partial positive-locking element engage optimally in the projections and/or recesses of the other positive-locking element, it is sufficient for transmitting the forces that are to be applied. However, if this is not the case, since the projections and/or recesses of the first partial positive-locking element are only engaged with the other recesses and/or projections of the other positive-locking element in the vicinity of the tips, for instance, the projections and/or recesses of one of the other partial positive-locking elements engages more effectively in the other positive-locking element. If the contact between the tips of the projections and/or recesses of the first partial positive-locking element and the tips of the projections and/or recesses of the other positive-locking element is not enough to securely transmit the acting forces, the two positive-locking elements "slip". However, after a relative movement of just a few degrees, this is absorbed by the projections and/or recesses of one of the other partial positive-locking elements, which engage better in the projections and/or recesses of the other partial positive-locking element due to the angular offset between the projections and/or recesses of different partial positive-locking elements.

The at least two partial positive-locking elements therefore preferably feature the same projections and/or recesses, in particular the same toothing, but offset from each other in the circumferential direction. The offset is preferably smaller than 10°, preferably smaller than 7°, especially preferably smaller than 5°. In this context, the same toothing means that the teeth have the same depth, the same flank profile and the same angular offset to each other.

In a preferred configuration, the at least two partial positive-locking elements are spaced apart from one another in the axial direction when the first positive-locking element and the second positive-locking element are not engaged with one another. In this way it is ensured which of the at least two partial positive-locking elements is the first partial positive-locking element to come into contact with other positive-locking elements.

In this case, a partial positive-locking element is shaped like a piece of pie. It preferably has two straight edges and one curved edge. It is preferably a segment of a circle. The toothing, which is preferably also shaped like a segment of a circle, is preferably situated on the front surface.

Preferably, the first joint element is an upper body element and the second joint element is an upper leg element. The device also features a pelvic element, wherein the two positive-locking elements can be brought in and out of engagement with one another by moving the upper body element relative to the pelvic element. This configuration of the invention is based on the knowledge that the lower back does not always need supporting when an angle between an upper body element, which is arranged, for instance, in the chest or back area of the upper body of the wearer, and the lower leg of the wearer is smaller than a predetermined angle, i.e. when the two body parts are swivelled against one another. Rather, support is only necessary when a swivelling occurs between the upper body, i.e. the chest, of the wearer, and the pelvis of the wearer. This configuration of the device thus ensures that a supporting force is always exerted when this swivelling between the upper body and the pelvis of the wearer occurs. Conversely, if the upper body swivels relative to the upper leg such that it does not cause a movement of the upper body relative to the pelvis, a force should not be exerted. In this case, the two gearwheels are not engaged with one another.

Preferably, at least two magnets are arranged on the pelvic element or the upper leg element and at least one magnet is arranged on the respective other element in such a way that they exert a force on one another, the direction of which changes when, during a movement of the upper body element relative to the pelvic element, the angle passes the predetermined limit angle. In this configuration, the displacement device thus features the magnets specified. On the element on the upper body element or the pelvic element on which two magnets are arranged, said magnets are preferably arranged in a different orientation. This means that for at least one of the magnets, the north pole is directed towards the respective other element of the orthopedic device and for at least one other magnet, the south pole is directed towards the respective other element.

If the angle between the upper body element and the pelvic element is greater than the predetermined limit angle, the two positive-locking elements are not engaged with one another. The magnets preferably cause the application of a force that keeps the two positive-locking elements apart. This may be achieved by the magnets exerting a force on one another. For example, this may be a repelling force.

This is achieved by positioning one magnet of the pelvic element and one magnet of the upper leg element close to each other, so that the same poles, i.e. the south pole or the north pole, are directed towards one another. If the pelvic element is now moved relative to the upper leg element, the magnets arranged on the respective elements are also moved. This results in a displacement of the moving magnets towards each other. At the point at which the angle of the upper body element relative to the pelvic element passes the predetermined limit angle, a second magnet of the pelvic element or the upper leg element preferably moves into the range of the at least one magnet of the respective other element. This results in an attractive force, as opposite poles of the two magnets are directed towards one another.

Preferably, at least some, but preferably all, projections and/or recesses of one of the positive-locking elements, but preferably of both positive-locking elements, feature undercut-toothing. This means that both flanks of a recess and/or projection are preferably tilted in the same direction. As a result, a torque can be applied to one of the positive-locking elements by the transmitted forces alone, which is converted into a force that has an axial component. This pulls the two positive-locking elements closer together, thus increasing the strength of the toothing, i.e. the engagement of the two positive-locking elements with each other.

The positive-locking elements can preferably be brought into engagement with each other by moving one of the positive-locking elements towards the other positive-locking element, which is mounted relative to the component on which it is arranged such that it can be rotated in one direction. The mounting is preferably a floating bearing, which allows a slight rotation of, for example, less than 15°, preferably less than 10°, particularly preferably less than 5°, thus ensuring that the optimum position and orientation of the two positive-locking elements relative to each other can be achieved.

The orthopedic device preferably features an upper body element, an upper leg element and a first passive actuator, which is configured to apply a force to the upper leg element and/or the upper body element when an angle between the upper leg element and the upper body element is within a first predetermined angular range. It is especially preferable if the device features at least a second passive actuator, which is configured to apply a force to the upper leg element and/or the upper body element when the angle is within a predetermined second angular range that is different to the first angular range.

The skilled selection of the first angular range and the second angular range allows the device according to the invention to be used, for instance, for both movement sequences described above. If the wearer of the orthopedic device bends only a little, for example, or works in a bent position, this preferably corresponds to the first angular range, so that the first passive actuator exerts the necessary force. However, if the wearer of the orthopedic device bends to pick something up off the ground, for instance, the resulting angle between the upper leg element and the upper body element preferably corresponds to the second angular range, so that the second passive actuator exerts the force.

The first and second angular range preferably overlap. In other words, there are angles between the upper leg element and the upper body element at which both passive actuators exert a force.

Preferably, the first passive actuator and/or the second passive actuator comprise(s) at least one mechanical energy store and/or one damper. For example, this can be an elastic element such as a spring element, preferably a tension spring. The first passive actuator and/or the second passive actuator may be designed to transmit a constant force across the respective angular range in which the respective actuator exerts the force. To this end, the respective actuator may have, for instance, a constant force spring. Alternatively or additionally, however, the actuator can also be designed in such a way that a force that increases as the angle decreases, rather than a constant force, is applied within the respective angular range. A decreasing angle means a more pronounced bend, so that in this case, the force exerted by the respective actuator increases the deeper the user of the device bends down. In another configuration, the force can also exhibit its maximum at an angle within the respective angular range and drop at larger angles and at smaller angles.

The first and second passive actuator are preferably designed to be different.

Specifically, the elastic elements of both actuators may exhibit different elasticities, in particular different spring constants, and/or different degrees of damping. In addition, they may also be different lengths, wherein the length of the elastic element is measured in the slackened state.

Preferably, the first passive actuator and/or the second passive actuator are arranged at at least one point of application on the upper leg element and/or the upper body element, each of which is adjustable. In this way, the respective predetermined angular range, within which the respective actuator exerts the force, can be adjusted. In addition, a preload of the respective passive actuator can be achieved, so that the size of the respective force to be applied can be adjusted.

To be able to apply different forces, it is advantageous if the first passive actuator and the second passive actuator are arranged at different points of application on the upper leg element and/or the upper body element and/or they have different lengths. As such, when the device is mounted, it is particularly easy to recognize which actuator exerts its force in which angular range and/or which actuator exerts a greater or smaller force. Of course, it is also possible to have both actuators strike at the same point of application or to use two actuators of the same length. This is possible, for example, if both actuators have different spring constants and/or elasticities.

In a preferred configuration, the upper body element features a first force transmission element and the upper leg element a second force transmission element. Both force transmission elements can be engaged with and disengaged from one another. The first mechanical energy store and the second mechanical energy store can be charged and discharged by swivelling the upper leg element relative to the upper body element, provided that the first force transmission element is engaged with the second force transmission element. Otherwise, the upper leg element and the upper body element can be swivelled against each other without charging one of the two mechanical energy stores with energy. This configuration renders it possible to swivel the upper leg element relative to the upper body element without charging the respective energy store with energy. In this state, no force is exerted by the energy store, i.e. the respective passive actuator. This is advantageous for certain movement sequences. If the user of the device climbs a step, for instance, he must raise his upper legs and therefore also the upper leg elements arranged on the upper legs. In other words, he has to swivel an upper leg element relative to the upper body element. If the two force transmission elements were engaged with one another in this state, raising the upper leg element would charge the mechanical energy store and extending the leg to the next step would discharge it again. However, if the device is not to provide support when climbing stairs, it is advisable to allow the two force transmission elements to disengage during this movement.

In many cases, the support offered by the orthopedic device should only be provided when lifting or standing up from a squatting position. To guarantee this, it must be ensured that the two force transmission elements only engage with each other in these states. This can be achieved, for example, by having a pelvic element and bringing the two force transmission elements into engagement with one another as soon as an angle between the pelvic element or a component of the pelvic element and the upper body element exceeds a predetermined limit angle.

The device therefore preferably has a pelvic element, wherein the upper body element is movably arranged relative to the pelvic element. In this case, the first force transmission element is engaged with and disengaged from the second force transmission element by moving the upper body element relative to the pelvic element. If the angle between the pelvic element and the upper body element gets reduced below a predetermined limit angle, the two force transmission elements are brought into engagement with each other. If the angle then exceeds the predetermined limit angle, the force transmission elements are disengaged again.

In preferred configurations, the first passive actuator and the second passive actuator are each arranged at one force application point on one force application lever. This is preferably arranged on the pelvic element or the upper body element. In these configurations, the two passive actuators preferably act on the upper leg element, i.e. they are arranged with one of their ends on the upper leg element and with the other end on the respective force application lever. If the two force transmission elements are disengaged, the force application levers can be freely swivelled relative to the pelvic element. If the upper leg element is swivelled relative to the pelvic element and thus also relative to the upper body element in this state, the force transmission levers follow this swivelling, such that the passive actuators and the mechanical energy stores preferably contained within them are not charged with energy. This results in no force and no support.

However, if the two force transmission elements do engage with each other, the force transmission levers are positioned on the pelvic element such that they are torque proof and can no longer follow the swivel movement of the upper leg element.

The distance between the force application point on the force application lever on the one hand and the point of application on the upper leg element on the other thus increases with the movement, so that the mechanical energy store is charged with mechanical energy and exerts a supporting force.

Preferably, an orientation and/or position of the two force transmission levers in relation to one another and/or at least one of the two, but preferably both, force application points is adjustable. The movement, for instance swivelling, of the two force application levers relative to each other enables the adjustment of the angular range in which the respective passive actuator exerts its force. A displacement of the force application point on the force application lever, for instance towards the swivel axis of the upper leg element relative to the pelvic element or away from it, enables the adjustment of the strength of the force to be applied. By adjusting the force application point on the force application lever differently, for instance in the circumferential direction with respect to the above-mentioned swivel axis, it is also possible to achieve a preload of the respective passive actuator.

A preload of the first actuator and/or a preload of the second actuator is preferably adjustable.

Preferably the pattern of the force applied by the first actuator and/or the force applied by the second actuator extends depends on the angle; in particular, said pattern is curved, especially preferably sinusoidal.

Preferably the force exerted by the first actuator and the force exerted by the second actuator exhibit a maximum at different angles.

For angles smaller than the respective predetermined angular, the force exerted by the respective actuator is preferably zero, or essentially zero. In this case, the more the upper body is bent relative to the upper leg, the smaller the angle.

Preferably, the first and second passive actuator each act on one force application lever. The two force application levers are preferably designed to be length-adjustable, so that the size of the torque applied by the respective actuator or the strength of the respective force can be adjusted. Additionally or alternatively, the force application levers are designed to be adjustable relative to each other and/or relative to a pelvic element so that the position of the predetermined first angular range and/or the position of the predetermined second angular range can be adjusted. When the upper body element bends relative to the upper leg element, the respective actuator, which can be a spring element for instance, is charged with mechanical energy and can thus exert the force. Here, the distance between the first end of the respective actuator and the second end of the actuator is greater.

The device preferably features an end stop, which can be arranged on a pelvic element, for example, and on which the first passive actuator and/or the second passive actuator strikes when the respective force application lever has reached a certain position, especially relative to the upper leg element. As a result, the respective actuator is still tensioned and charged with mechanical energy, but said energy preferably acts directly on the rotational axis between the upper body element and the upper leg element, provided that the end stop is arranged on this rotational axis. A force is thus exerted but it no longer leads to a torque; therefore, it also does not lead to a support of the back. The orthopedic device for supporting a lower back of a user comprises at least one mechanical energy store, a pelvic element, a torso element and an upper leg element, wherein the mechanical energy store can be charged and discharged by swivelling the upper leg element relative to the torso element. Preferably, the upper body element is arranged on the pelvic element by means of two rail elements, wherein the rail elements are each arranged with a first end on the pelvic element such that they can swivelled about at least a first swivel axis and with a second end opposite the first end on the upper body element such that they can be swivelled about at least a second swivel axis.

The pelvic element is preferably designed as a pelvic harness or hip harness and therefore extends fully around the body at the height of the pelvis or hips. Between the two first ends of the two rail elements, which are arranged on the pelvic element, extends a part of the pelvic element, which is preferably not or at least largely not variable in length when the device is in use. In a structurally simple and therefore preferred configuration, the distance between the first end and the second end of the respective rail element is also designed to be not or at least largely not variable in length when the device is in use. This also applies for the distance between the two second ends of the rail elements. This results in a parallelogram which, due to the articulated arrangement of the respective parts, is movable. In a preferred embodiment, the freedom of movement of the user's upper body and in particular the user's spinal column is not or at least largely not restricted.

Preferably, at least one of the specified variables is designed to be adjustable. The respective variable can therefore be adjusted to fit a body part of the user. After adjustment, it is set to the individually desired value and then fixed, e.g. locked, in such a way that it does not change or at least largely does not change when the device is used. It is preferable if several, but especially preferable if all, specified variables can be adjusted and locked in this manner.

It is particularly preferable if the upper body element is arranged on the pelvic element in such a way that the lateral flexion of the spinal column and the rotation of the spinal column about a rotational axis in the sagittal plane is possible. In this case, the freedom of movement of the spinal column of the user is not restricted at all, so that all movements that the user of the orthopedic device can execute with his spinal column without the orthopedic device are also possible with the orthopedic device.

A rotational axis in the sagittal plane is understood particularly to mean a vertical rotational axis which lies in the median plane, and thus in the central sagittal plane, when a user is standing up straight. It could also be described as the longitudinal axis of the spinal column, wherein the spinal column of a human, due to its geometric form, does not have a longitudinal axis in the mathematical sense. Of course, rotational axes displaced parallel to this axis also lie in a sagittal plane.

If the freedom of movement of the user's spine is not restricted by the device, it is understood particularly to mean that both flexion and extension are possible. These movements are also referred to as ventral flexion and dorsal extension, or inclination and reclination. A flexion is the leaning forward of the upper body, and thus of the spinal column and the head, while extension is the opposite movement. In this case, other movements of the upper body and therefore the spinal column, such as lateral flexion and rotation, are also not restricted by the orthopedic device.

Movements of the spinal column, particularly a leaning of the spinal column to the side and/or forwards and backwards and/or a twisting of the spinal column about its longitudinal axis, are preferably also not prevented, restricted or rendered impossible by the orthopedic device. All of the movements described here are preferably restricted by the orthopedic device in neither their maximum movement deflection nor in a sequence of movement.

If the upper leg element is swivelled relative to the upper body element in a first direction, the mechanical energy store, which can be, for instance, an elastic element such as a tension spring, is charged with energy. The first direction corresponds, for example, to raising the upper leg element, for instance to climb a step. However, it is preferable to have the device in a deactivated state when climbing stairs, so that no supporting force is applied when climbing stairs. Bending forward (flexion) of the upper body also swivels the upper body element relative to the upper leg element accordingly. The first direction is thus characterized in that an angle between the upper leg element and the upper body element decreases due to the swivelling.

The energy that charges the mechanical energy store can be, for instance, an elastic or potential energy. In this state, the mechanical energy store preferably applies a force to the upper leg element and/or the upper body element which acts in the second direction that is opposite to the first. If the upper leg element is swivelled relative to the upper body element in this second direction, the mechanical energy store is discharged and the energy released supports the movement of the upper leg element relative to the upper body element. This second direction refers, for instance, to the lowering of the upper leg element or an extension of the leg, or a straightening (extension) of the upper body. In all these movements, the upper leg element is swivelled relative to the upper body element in the second direction.

If the user of the orthopedic device wants to lift a heavy object, for example, he bends his knees and grabs the object. Here, both upper legs and therefore also the respective upper leg element are swivelled relative to the upper body and thus to the upper body element in the first direction. The angle between the upper leg and the upper body decreases. This causes the mechanical energy store to be charged with potential energy. To lift the object, the user of the orthopedic device must now extend his legs, wherein the upper leg is swivelled relative to the upper body in the opposite second direction. The potential energy stored in the mechanical energy store is released and supports the corresponding movement.

Preferably, the first swivel axes extend at least largely in frontal planes, but preferably in a common frontal plane. It is especially preferable if the first swivel axes extend through the hip joint of the user, so that the first ends of the rail elements are arranged laterally, i.e. externally. Conversely, the second ends of the rail elements are arranged dorsally, i.e. at the back, on the upper body element. The rail elements preferably extend in such a way that the first end is rotated by 90° relative to the second end. Here, the rail elements are preferably configured and arranged to be mirror-symmetrical to one another.

The second swivel axes preferably extend at least largely in the sagittal plane. Here, it is especially preferable for them to extend from dorsal to ventral, i.e. from back to front. As a result, an inclination of the body and the spinal column to the side is also possible without restricting the freedom of movement.

In a preferred configuration, the rail elements feature at least two partial rails, which are arranged on each other such that they can be swivelled about a third swivel axis. The three swivel axes preferably extend largely in sagittal planes. It is especially preferable if, when the orthopedic device is mounted, they extend largely parallel to the second swivel axes when the user of the orthopedic device stands upright. The swivel joints, which enable a movement of the partial rails relative to one another, are preferably arranged closer to the first end than the second end of the respective rail elements. It is especially preferable if these joints are positioned to the side of the body of the user, so that an imagined extension of the third swivel axis leads past the user's body.

When the orthopedic device is mounted, the second ends of the rail elements are preferably arranged in the region of the shoulder blades, but especially preferably in the region of the lower angles of the user's shoulder blades. When the spinal column bends right or left, this region exhibits the starkest deviation from a straight line, so that the joints, which connect the second ends to the upper body element in this region, are optimally positioned.

In a preferred configuration, a distance between joints, with which the second ends of the rail elements are arranged on the upper body element, is adjustable. The joints are preferably arranged on the upper body element such that they can be displaced. This is achieved, for instance, by arranging the respective joint on a slider that can be displaced along a guide, such as an elongated hole or link arranged in or on the upper body element.

Preferably, the second ends of the rail elements are arranged on the upper body element in such a way that they can be swivelled about two different swivel axes, one of which preferably extends in the dorsal-ventral direction and the other in the medial-lateral direction. The first of these two swivel axes allows the user of the orthopedic device to incline his upper body to the right and left, while the second of the two swivel axes is required to bend the user's upper body forwards or backwards.

In preferred embodiments, the two ends of the rail elements are arranged on the upper body element by means of ball joints. As a result, freedom of movement is further increased, as is the degree of acceptance of the orthopedic device by the user.

When the orthopedic device is mounted, the upper body element preferably extends completely around the user's upper body. It is preferably designed to be so dimensionally stable that its diameter in the medial-lateral direction does not or largely does not change when the upper body bends over. If the at least one mechanical energy store is to be charged with energy, the upper body element must be swivelled relative to the upper leg element. Where applicable, an activation device must also be activated, which may be achieved, for instance, via a movement of the upper body element relative to the pelvic element. If the energy store, which comprises a spring element for example, is charged, a force must be exerted, which can be caused by the upper body bending over. In the examples of embodiments specified, the upper body then exerts a tensile force on the upper body element.

The upper body element preferably comprises a chest section which, when the orthopedic device is mounted, rests on the user's chest at at least two spaced points on different sides of the user's sternum. The force is transmitted via these points from the upper body to the upper body element. Of course, this is also possible if the upper body element only comes into contact with the user's chest at a single point or at more than two points. To charge the energy store with energy, a tensile force is exerted on the upper body element via the upper body and thus via the user of the orthopedic device. When the energy store is discharged, a tensile force is exerted on the upper body via the upper body element; said tensile force acts to support the user's lower back, for instance when straightening up. In this case, the tensile force is preferably transmitted via the rail elements to the upper body element and from here to the upper body. Since the rail elements are arranged dorsally, i.e. on the user's back, the tensile force is transmitted to the dorsal section of the upper body element and from there to the frontal section of the upper body element. This tensile force is transmitted to the upper body via the points at which this frontal section comes into contact with the upper body, i.e., preferably to the right and left of the user's sternum. Sufficient dimensional stability ensures that there is no constriction of the user's upper body when the tensile force is applied to the dorsal part of the upper body element. If the dimensional stability is too small, it is actually transferred to the upper body from frontal to dorsal through the parts of the upper body element that pass the sides of the upper body, like a sling to which a tensile force is applied.

In this case, part of the force is transferred into a medially acting force, which can have painful effects.

Preferably, the part of the upper body element that surrounds the upper body is not completely dimensionally stable; rather, it exhibits a small degree of flexibility and preferably elasticity. This ensures that the orthopedic device and the upper body element is suitable for different people with different chest measurements, and can be designed to allow for the adjustment of this variable. It may be sufficient to connect individual rigid and inflexible elements to one another in a flexible and preferably elastic way, e.g. using half-shells or shell elements that surround parts of the upper body in a dimensionally stable and rigid manner. Alternatively, the upper body element can also be designed without any rigid elements.

In a preferred configuration, the orthopedic device features a first and a second upper leg element, and a first and a second mechanical energy store. Here, the first mechanical energy store can be charged and discharged by swivelling the first upper leg element relative to the upper body element. The second mechanical energy store can be charged and discharged by swivelling the second upper leg element relative to the upper body element. This configuration enables independent movement of the upper leg relative to the upper body element. The mechanical energy store only applies a force to the upper leg which has been swivelled relative to the upper body element.

Preferably, every upper leg element is arranged on the pelvic element by means of a joint arrangement such that it can be swivelled about a joint axis. The joint arrangement is preferably positioned in such a way that the joint axis extends through a hip joint of the user.

The upper leg element preferably features at least one mounting element for mounting it on the upper leg and at least one compressive force transmission element, via which the mounting element is connected to the joint arrangement.

In a preferred embodiment, the compressive force transmission element is a rod or rail; it is particularly preferable if it is ergonomically formed.

The mounting element is preferably connected to each joint arrangement by at most one compressive force transmission element.

It is advantageous if each of the rail elements used is arranged on the upper body element such that it can be swivelled about at least two swivel axes, wherein at least two of the swivel axes are preferably perpendicular to each other.

It is particularly preferable if at least one of the rail elements is arranged on the upper body element via a ball joint. All rail elements are preferably each arranged on the upper body element via one ball joint.

Preferably at least one rail element, but especially preferably every rail element, is arranged on the respective joint arrangement, which is arranged on the pelvic element, such that it can swivelled about an axis of movement, wherein the axis of movement is preferably perpendicular to the joint axis of the respective joint arrangement.

The various movable configurations are designed so that the movements of the user's upper body, and in particular the spinal column, can be followed and, irrespective of the position of the upper body element relative to the pelvic element and/or relative to the at least one upper leg element, the force applied by the mechanical energy store in the charged state can act.

In an especially preferred configuration, the at least one rail element is designed to be adjustable in length. It is particularly preferable if all rail elements are adjustable in length. The orthopedic device can thus be used for people of different sizes. The length-adjustable rail element can preferably be fixed at different length settings, so that the length can be adjusted but then remains unchangeable.

The mechanical energy store preferably comprises at least a spring element, a pressure accumulator, a pneumatic and/or hydraulic system and/or a hydraulic energy store. Elastic elements in the form of elastic cords, such as rubber cords, are also conceivable. Of course, other elements, such as gas springs or compression springs, are also conceivable, for which a deflection is used to transform the compressive force coming from the compression spring into a tensile force. mechanical energy store can be arranged at various positions on the device. Preferably, a position is selected at which the installation space required for the energy store is available and the energy store does not cause any disruption, even while the user's leg is moving. For instance, it may be arranged on the upper leg.

For arranging the upper body element on the user's upper body, a shoulder element for mounting on the shoulder, which can be in the form of rucksack straps or braces, for example, is particularly suitable. It allows for an especially small design of the orthopedic device.

The upper leg element preferably comprises an upper leg shell that is preferably arranged on a spacer element. This spacer element, as part of the upper leg element, is preferably connected to the pelvic element. The lengths of the compressive force transmission element, which is designed as a rail or rod for example, and where applicable of the spacer element, which is also designed as a rod or rail, are preferably selected such that the entire angular range of the potential movement of the wearer's lower leg is covered. The upper leg shell is preferably flexibly arranged on the spacer element to render the device as comfortable as possible to wear.

In a preferred configuration, the passive actuator is configured to generate a force, irrespective of a position and/or orientation of the at least one leg support element relative to the pelvic element and/or the upper body element.

In a preferred configuration, the upper leg shell for mounting on the user's upper leg is preferably arranged on the upper leg element, but preferably on each upper leg element. Said shell is preferably designed to be padded to render it as comfortable as possible to wear. The upper leg shell is preferably arranged by means of a ball joint. This ensures the greatest possible freedom of movement in relation to the rest of the device, which is particularly advantageous when the user moves. By means of the ball joint, the upper leg shell can be arranged directly on a rail element or spacer element of the upper leg element. Alternatively, it is positioned on a holding bracket.

The upper leg shell can preferably be swivelled relative to the upper leg element about a rotational axis, preferably against a force of a spring element, wherein the rotational axis preferably extends in the medial-lateral direction. This is rendered particularly feasible by way of the positioning of the upper leg shell on the holding bracket, which is arranged on another component of the upper leg element such that it can be swivelled about the rotational axis.

BRIEF DESCRIPTION

In the following, some examples of embodiments of the present invention will be explained in more detail by way of the attached figures.

FIG. 1 schematically depicts various elements of an orthopedic device according to an example of an embodiment of the present invention. It shows a first positive-locking element, which is designed as a first gearwheel 2, which can be displaced along guide rods 4 on the component on which it is arranged. It is displaced along these guide rods 4 when the first gearwheel 2 is to be engaged with the second positive-locking element, which is designed as a second gearwheel 6. The first gearwheel 2 and the second gearwheel 6 feature schematically indicated teeth 10 on their end faces 8, which are designed to correspond to each other. A guide spindle 12 protrudes from the end face 8 of the second gearwheel 6 in the axial direction, meaning parallel to the axis "AX" about which the first gearwheel 2 and thesecond gearwheel 6 can rotate as described herein. In the FIG. 1 example, teeth are arranged on the end face 14 of the guide spindle 12. The toothing on the end face 14 of the guide spindle 12 corresponds to the toothing on the end face 8 of the second gearwheel 6. A toothing is also arranged on a lateral surface 16 of the guide spindle 12, which ensures that the guide spindle 12 is set in rotation about axis AX when the guide spindle 12 is moved in the axial direction with respect to the second gearwheel 6 until it is received in the second gearwheel 6.

When the first gearwheel 2 is moved along the guide rods 4 towards the second gearwheel 6, the teeth of the end face 14 of the guide spindle 12 first engage with the teeth 10 of the end face 8 of the first gearwheel 2. The guide spindle 12 is then pushed into the second gearwheel 6 and set in rotation, shown due to the teeth of the lateral surface 16. The first gearwheel 2 is mounted so that it can follow the only slight rotation of the guide spindle 12, so that it reaches the optimum position relative to the second gearwheel 6 as soon as the guide spindle 12 is received in the second gearwheel 6.

Figure 2:
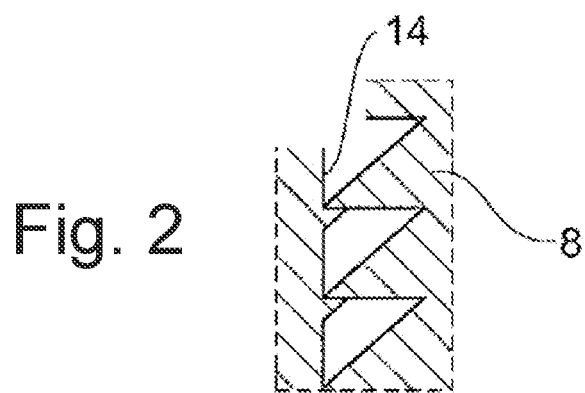

FIG. 2 schematically depicts an embodiment of the various teeth. It shows the end face 14 of the guide spindle 12 on the left and the end face 8 of the first gearwheel 2 on the right. The very differently shaped teeth ensure that, regardless of the position in which the first gearwheel 2 meets the guide spindle 12, the respective teeth always engage with each other.

Figure 3:
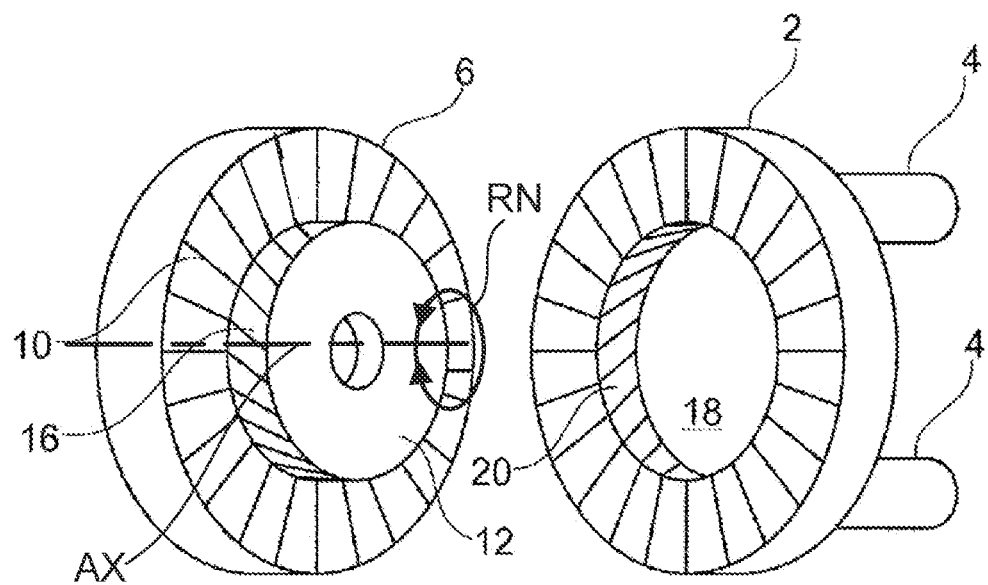

FIG. 3 shows another configuration. The first gearwheel 2 has a central bore 18, the inner wall 20 of which features grooves or a toothing, which can also be designed as internal thread. The toothing on the lateral surface 16 shown in FIG. 1 can also be designed in the form of an outer thread. In the example of an embodiment shown in FIG. 3, the second gearwheel 6 features a guide spindle 12; however, it is not arranged such that it can be displaced relative to the second gearwheel 6. Instead, the lateral surface 16 of the guide spindle 12 is designed with an outer thread which is designed to correspond to the inner thread of the internal wall 20 of the central bore 18. If, in this configuration, the first gearwheel 2 is moved along the guide rods 4 towards the second gearwheel, the outer thread of the lateral surface 16 engages in the inner thread of the inner wall 20 of the central bore 18 of the first gearwheel 2.

Further displacement of the first gearwheel 2 towards the second gearwheel 6 causes a rotation of the first gearwheel 2 relative to the second gearwheel 6, which again ensures that the teeth 10 of the first gearwheel 2 engage as optimally as possible in the teeth 10 of the second gearwheel 6.

Figure 4:
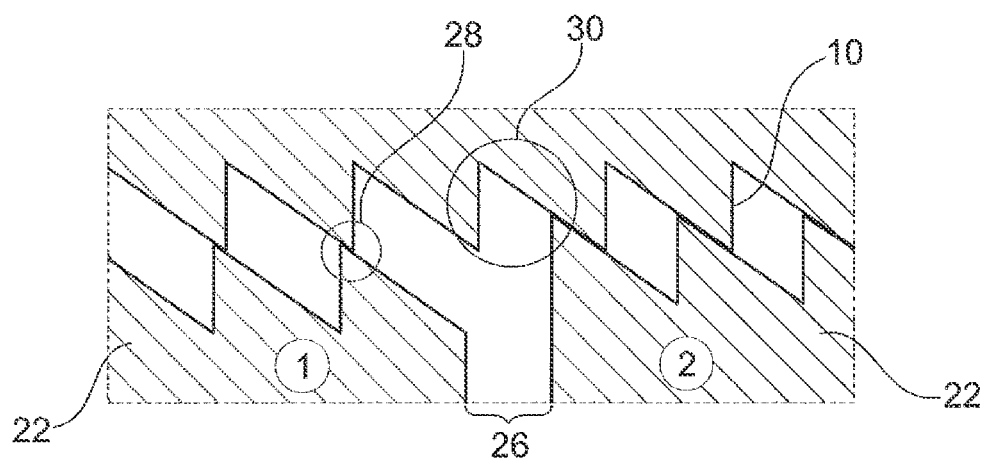
FIG. 4 —schematically depicts parts of a safety device according to an embodiment providing gearwheels comprising partial gearwheels arranged co-axially.
Figure 5:
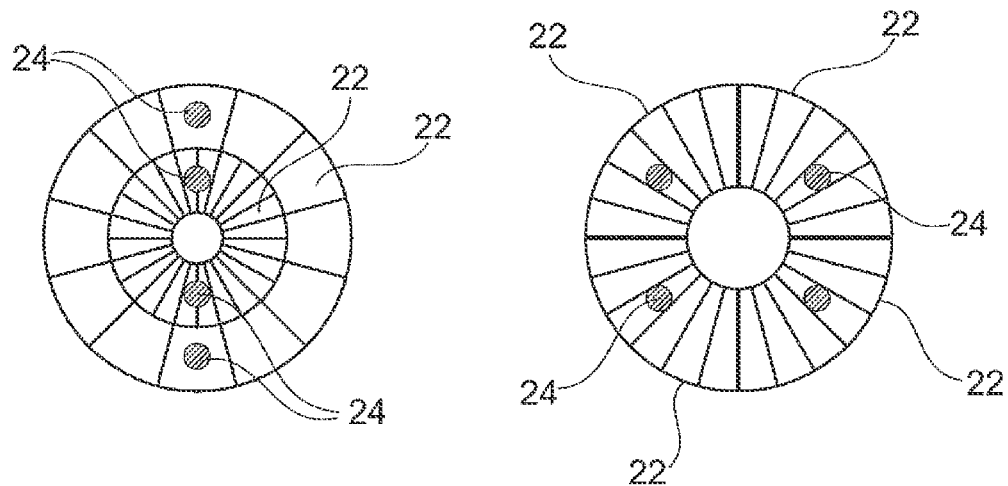
FIG. 5 —schematically depicts parts of a safety device according to a variation of the FIG. 4 embodiment, providing partial gearwheels arranged co-axially.

FIGS. 4 and 5 depict a schematic representation of parts of a safety device, one of the gearwheels of which comprises partial gearwheels. In the left-hand area of FIG. 5, one of the gearwheels features two partial gearwheels 22, which are arranged co-axially. The partial gearwheels 22 are arranged via schematically depicted elastic elements 24 in the axial direction, i.e. perpendicular to the drawing plane, such that they can be displaced. The teeth of the partial gearwheels 22 are arranged at a slight offset to each other. In particular, the offset is preferably half a tooth length. If a gearwheel now engages in the teeth of these partial gearwheels 22, which preferably protrude to different degrees in the axial direction, the situation shown in FIG. 4 occurs. The partial gearwheels 22 each have teeth which are separated from each other by the offset 26 and therefore engage to different extents with the teeth 10 of the respective other gearwheel. In the area 28 there is only very little contact between the teeth of the partial gearwheel 22 and the teeth 10 of the respective gearwheel. If the force to be applied is too great, the teeth slip off each other at this point. However, the two components can only be moved against each other until, in the area 30, the teeth of the other partial gearwheel 22 are engaged with the teeth 10 of the gearwheel. Since the partial gearwheels 22 are displaced against each other in the axial direction, the teeth of the different partial gearwheels engage with the teeth of the gearwheel to different extents.

Figure 6:
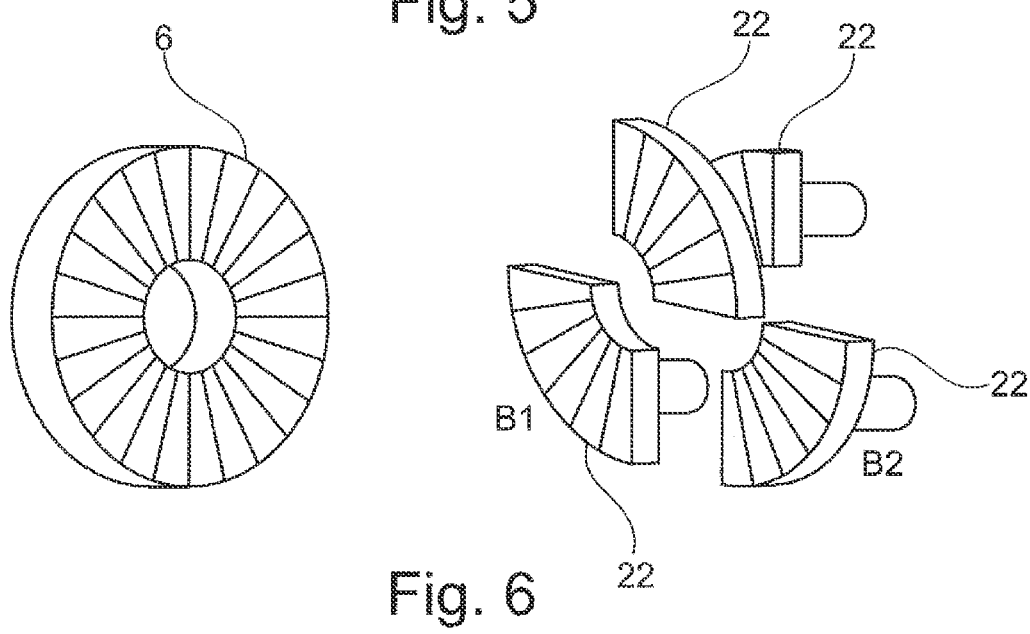
FIG. 6—schematically depicts a combination of a gearwheel comprising four partial gearwheels 22 in combination with a one-piece spur gearwheel.

In the right-hand section of FIG. 4, the gearwheel features four partial gearwheels 22, each of which is elastically mounted in the axial direction via an elastic element 24. FIG. 6 schematically depicts a combination of a first gearwheel 2 comprising four partial gearwheels 22 and a second gearwheel 6, which is a simple spur gearwheel. The four partial gearwheels 22 correspond to the arrangement shown in FIG. 5 and are arranged in the axial direction at a stark offset and not true to scale.

Figure 7:
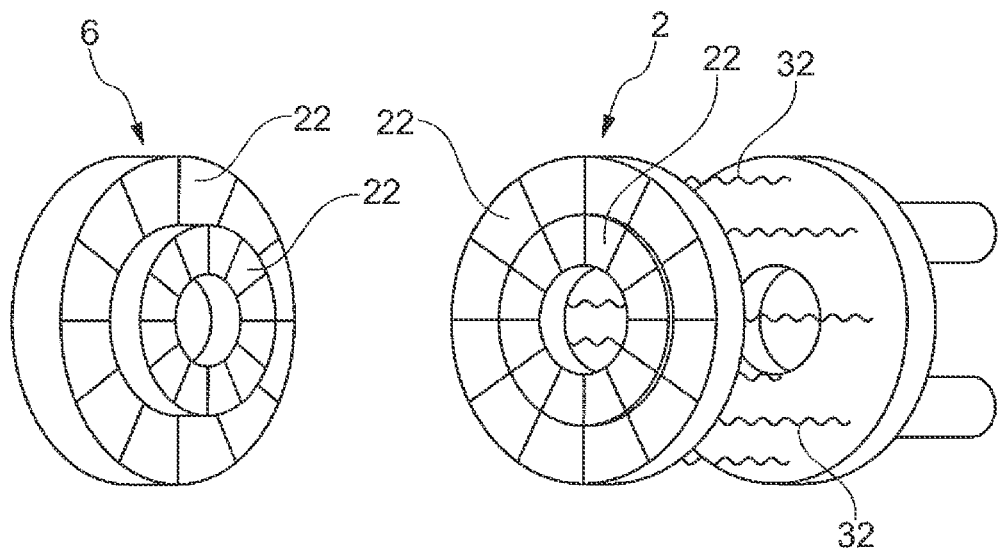
FIG. 7 —schematically depicts another configuration in which a gearwheel has two partial gearwheel, an inner and an outer partial gearwheel.

FIG. 7 shows another configuration, wherein the second gearwheel 6 has two partial gearwheels, which are shown as a second inner partial gearwheel 22A and a second outer partial gearwheel 22*b* (collectively "second gearwheel 6 partial gearwheels 22") arranged axially at a slight offset to each other, but fixed to each other.

The first gearwheel 2 of the FIG. 7 embodiment also features two partial gearwheels, comprising a first inner partial gearwheel 23A and a first outer partial gearwheel 23B (collectively "first gearwheel partial gearwheels 23" which, like the second gearwheel 6 partial gearwheels 22, are arranged coaxially to each other and can be axially displaced via indicated spring elements 32. In the embodiment shown, if the first gearwheels 2 and the second gearwheel 6 as depicted are moved towards each other, the first inner partial gearwheel 23A initially engages in the teeth of the second inner partial gearwheel 22A.

Only when the first gearwheel 2 is axially displaced further in the direction of the second gearwheel 6 do the first and second outer partial gearwheels 23B and 22B engage with each other. Due to the offset toothing, the schematically depicted situation in FIG. 4 occurs. If the engagement of the first and second inner partial gearwheels 23A and 22A with each other corresponds to the situation shown in area 28, it is ensured that the outer partial gearwheels 22 engage with each other according to the situation shown in area 30 of FIG. 4.

Figure 8:
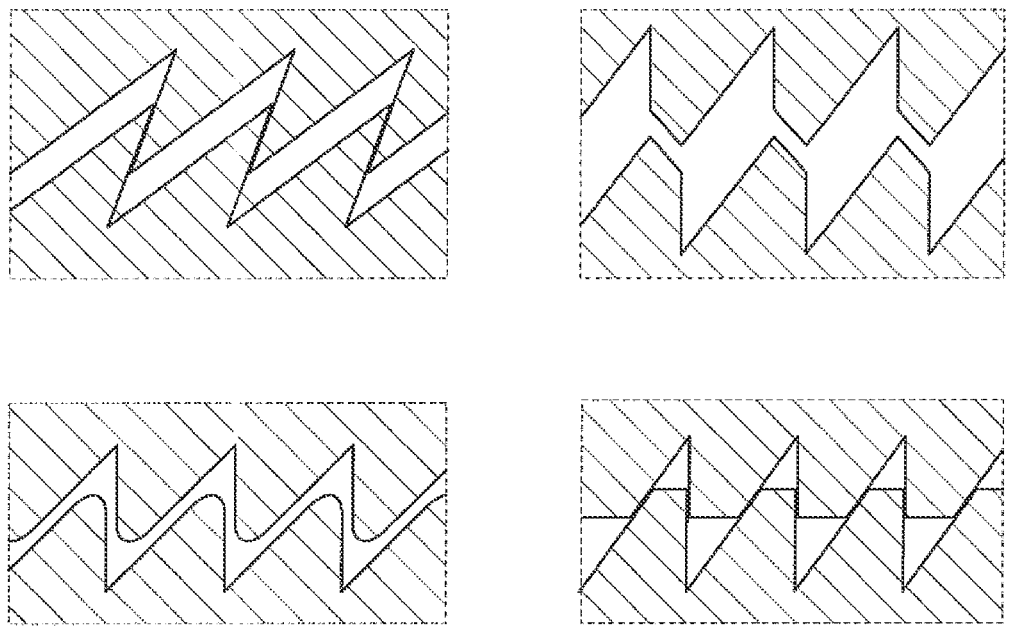
FIG. 8 —schematically depicts various forms of teeth that can be used with various described embodiments.

FIG. 8 depicts various forms of tooth that can be used.

Figure 9:
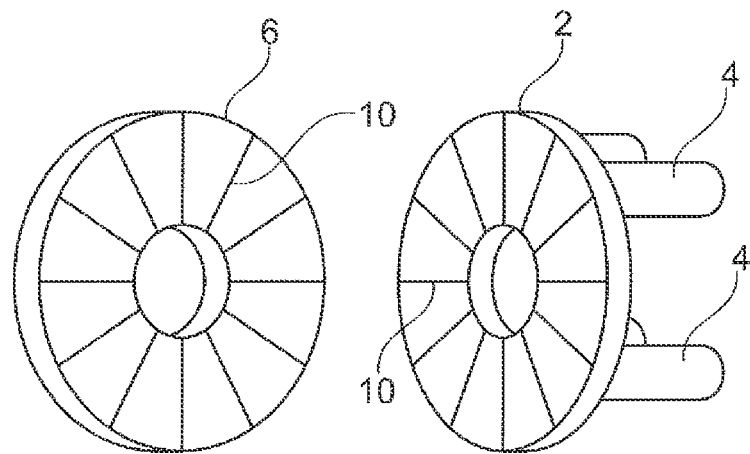
FIG. 9—schematically depicts, in accordance with various embodiments, the FIG. 1 first gearwheel and second gearwheel with teeth configured as undercut toothing.

FIG. 9 shows the first gearwheel 2 and the second gearwheel 6 as shown in FIG. 1. Again, the first gearwheel 2 is arranged such that it can be displaced along the guide rods 4. In the example of an embodiment shown, the teeth 10 are designed as an undercut toothing.

Figure 10:
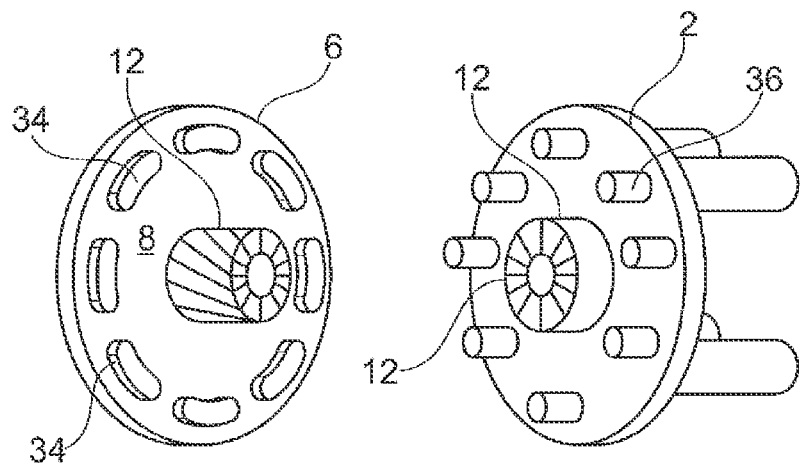
FIG. 10 —schematically depicts an example in accordance with various embodiments, including a first and second gearwheel each having a guide spindle, with respective frontal projections and/or recesses that engage with one another them.

In FIG. 10, the first gearwheel 2 and the second gearwheel 6 each have a guide spindle 12. Each guide spindle protrudes from the respective gearwheel 2, 6 at the front. The two guide spindles 12 have frontal projections and/or recesses which can be brought into engagement with one another. Instead of the toothing shown in the other figures, there are elongated holes 34 in the end face 8 of the second gearwheel 6, which are designed in such a way that pins 36, which protrude from the end face of the first gearwheel 2, can engage in them.

Figure 11:
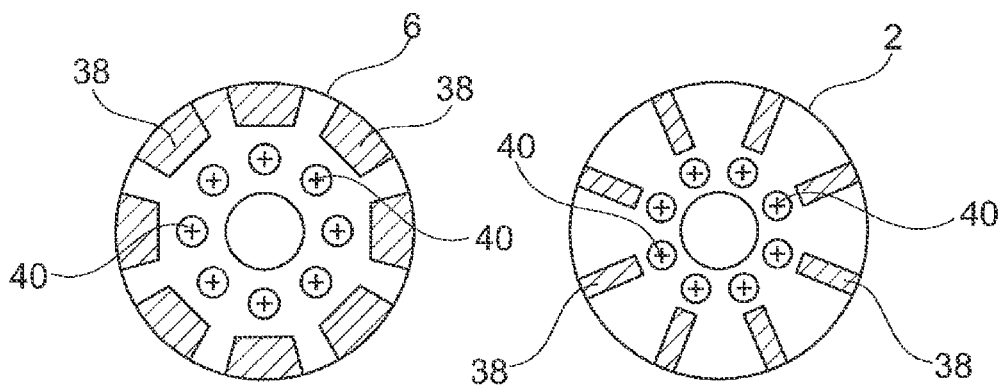
FIG. 11 —schematically depicts shows the end faces with magnets arranged in accordance with various embodiments.

FIG. 11 shows the end faces of the first gearwheel 2 and the second gearwheel 4, which each feature projections 38 between which recesses are arranged, so that the projections 38 of the two gearwheels can engage with each other. Magnets 40 are shown schematically in the central area of the end faces, wherein said magnets are arranged in such a way that poles of the same name are directed towards each other. This produces a repellent effect, which is minimal if the magnets 40 of one gearwheel, preferably arranged equidistantly, are placed exactly between the magnets of the other gearwheel. The two gearwheels 2, 6 can also be aligned in relation to one other in this way.

Figure 12:
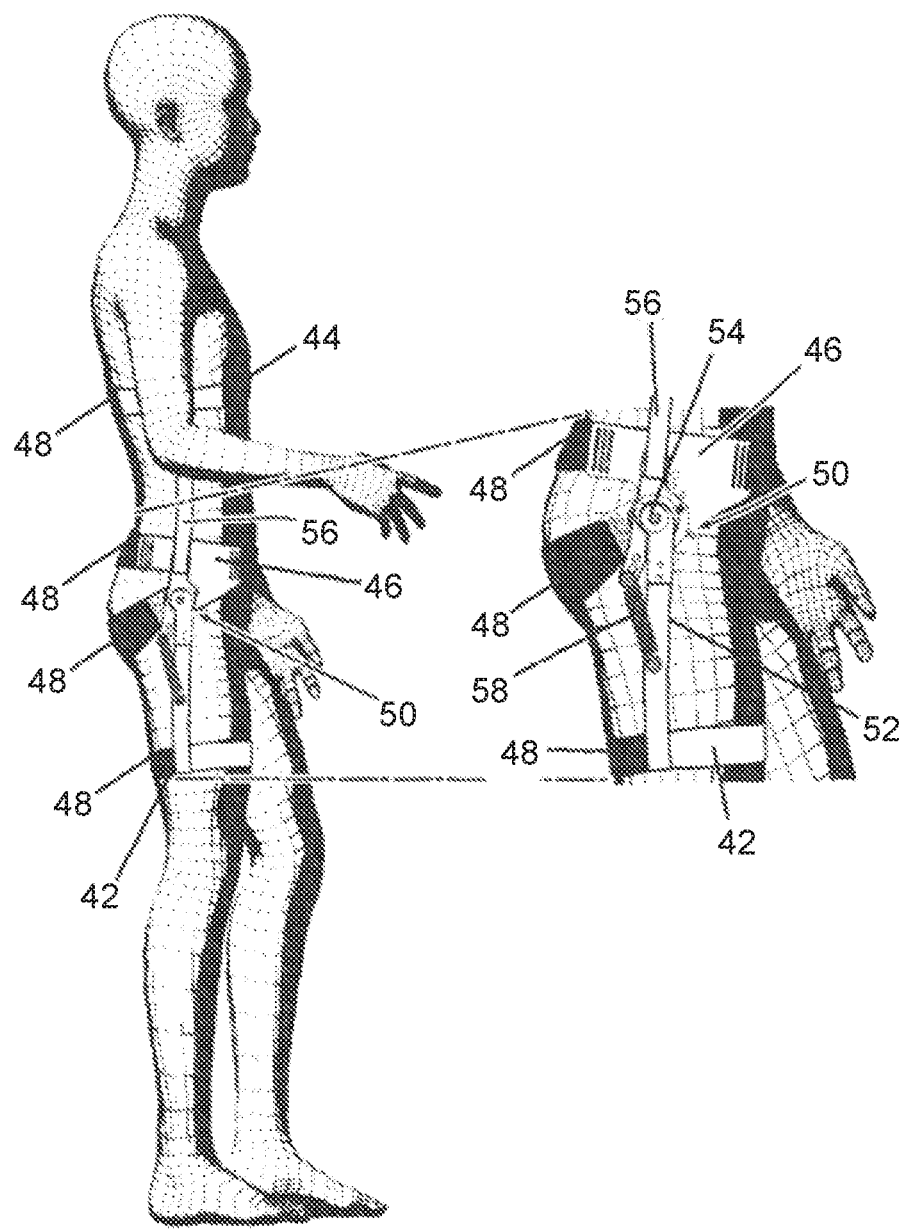
FIG. 12—schematically depicts an orthopedic device according to a first example of an embodiment of the present invention in the applied state.

FIG. 12 shows an orthopedic device in an applied state, with which structures shown in FIGS. 1-11 may be used. The FIG. 12 device comprises an upper leg element 42, which is arranged on an upper leg of the user, and an upper body element 44, which is arranged on the upper body. The device also features a pelvic element 46, which is arranged on the pelvis of the user. Both the pelvic element 46 and the upper leg element 42 as well as the upper body element 44 are arranged on the respective body part of the user. The orthopedic device also has a joint device 50, which performs several functions in the example of an embodiment shown. On the one hand, the upper leg element 42 is arranged about a first swivel axis 54 on the pelvic element 46 via a first splint 52. The upper body element 44 is also arranged on the pelvic element 46 via a second splint 56 such that it can be swivelled, wherein the swivel axis coincides with the first swivel axis 54 in this example of an embodiment.

The orthopedic device also has a mechanical energy store 58, which is a tension spring in the example of an embodiment shown.

Figure 13:
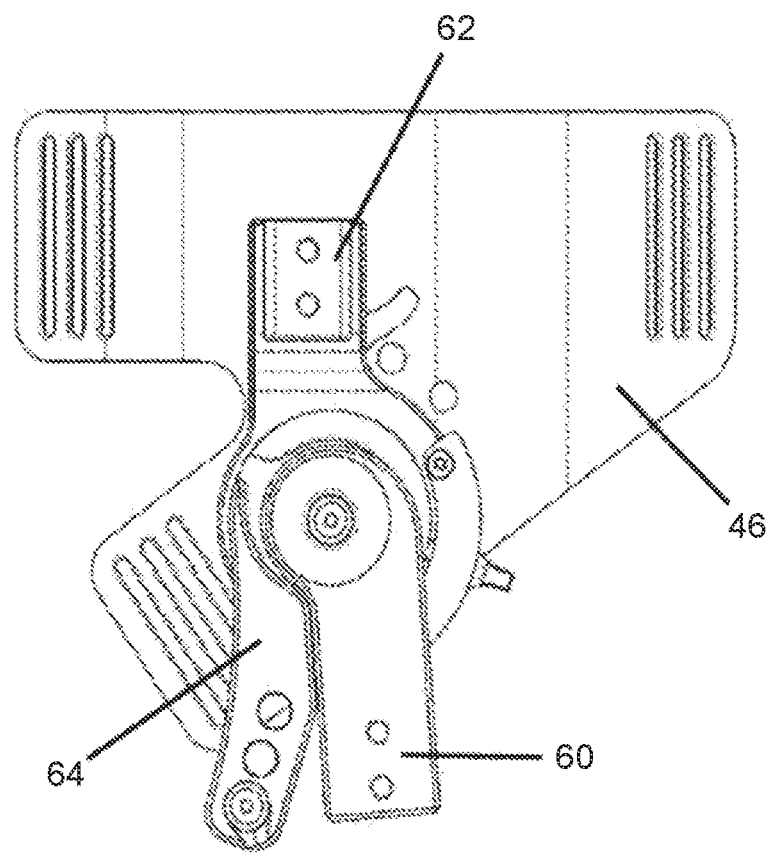
FIG. 13—schematically depicts a section of the orthopedic device in a view.

FIG. 13 depicts an enlarged representation of the pelvic element 46. One recognizes a first connection element 60, on which the first splint 52 of the upper leg element 42 is to be arranged, and a second connection element 62, on which the second splint 56 of the upper body element 44 is arranged. A lever 64 is provided, on which the mechanical energy store 58 is positioned.

Figure 14:
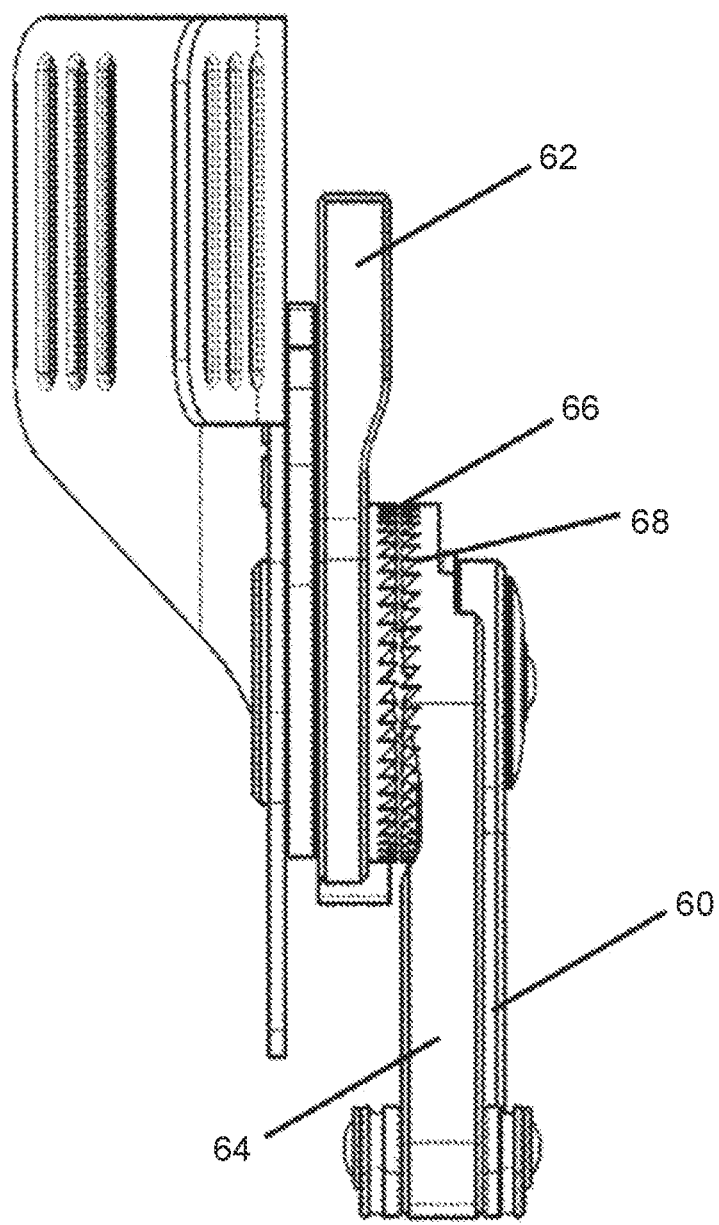
FIG. 14—schematically depicts a section of the orthopedic device in another view.
Figure 15:
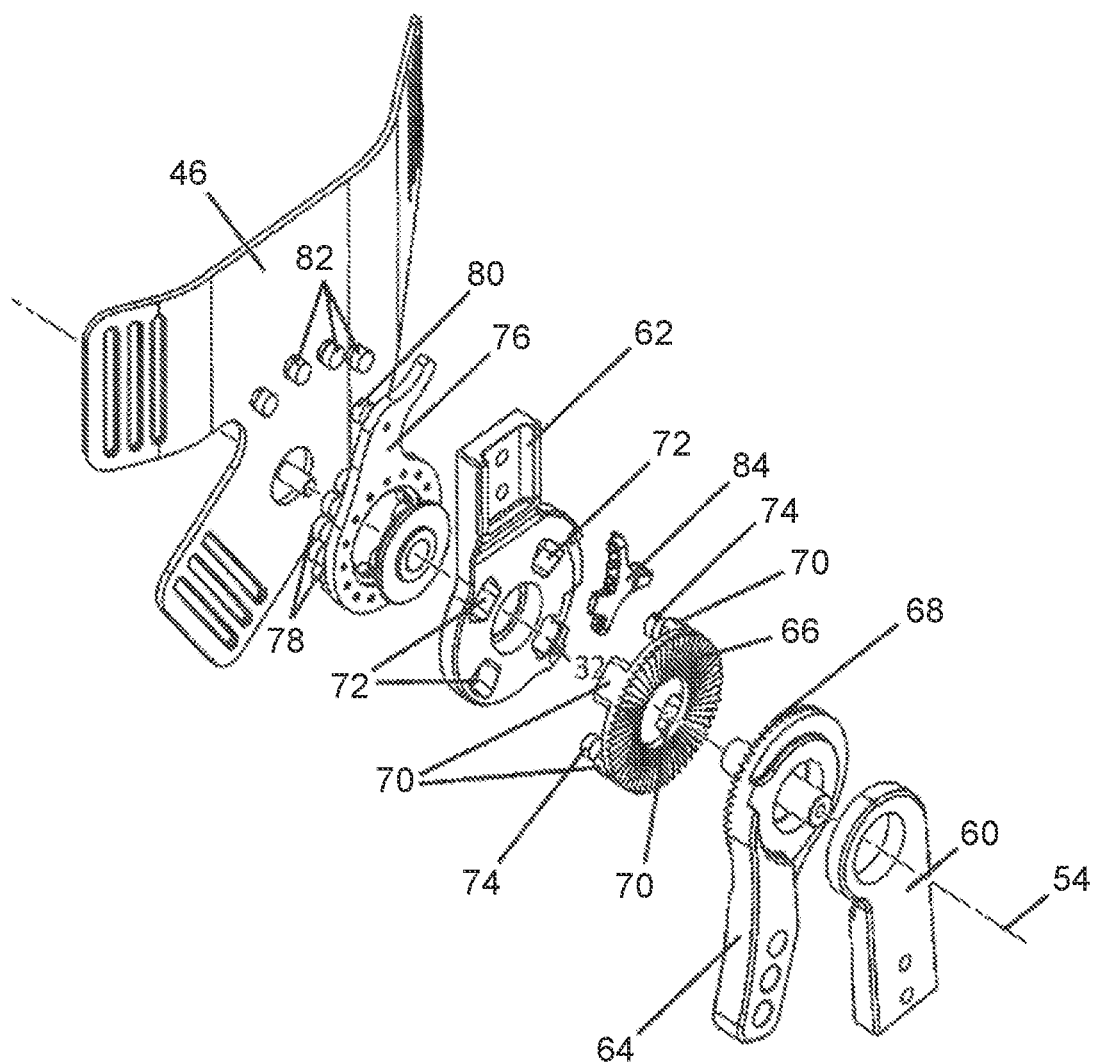
FIG. 15—is an exploded representation of the section from FIGS. 13 and 14.

FIG. 14 depicts a side view of the device from FIG. 13. A first force transmission element 66, which is designed as a front gearwheel in the example of an embodiment shown, is situated on the second connection 62, which forms part of the upper body element 44. A corresponding second force transmission element 68 is positioned on the lever 64, which forms part of the upper leg element 42. The exploded view in FIG. 15 shows how it functions. The second force transmission element 68 is situated on the lever 64. The first force transmission element 66 is found as a separate component on the second connection element 62. The first force transmission element features four projections 70, which engage in four specially provided openings 72 on the second connection element 62. In FIG. 15, it can be recognized that a magnet 74 is arranged on two of the projections 70, wherein said magnet protrudes through the respective openings 72 when in the applied state. A displacement device 76 is arranged on the actual cover element such that it is torque-proof. The displacement device 76 also comprises a series of magnets 78. In the example of an embodiment shown, the magnets 78 extend across the entire circumference of the displacement device 76, thereby affecting the magnets 74 on the first force transmission element 66. At the upper end of the displacement device 76 shown in FIG. 15, a positioning magnet 80 is depicted, which interacts with corresponding counter-magnets 82 that are arranged on the pelvic element 46. The positioning magnet 40 and the counter-magnets 42 are arranged such that opposite poles are directed towards one another. In the example of an embodiment shown, the displacement device 76 can thus be fixed on four different positions relative to the pelvic element 46 such that it is torque-proof.

If the upper body element 44 and therefore the second connection element 62 is now twisted relative to the pelvic element 46, the position of the magnets 74 relative to the magnets 78 also changes. These are arranged in such a way that at a certain angle, at which the upper body element 44 is twisted relative to the pelvic element 46, the polarity of the magnets 78 changes, so that an attractive force acts between the magnets 74 and 78 up until this angle and a repelling force acts from this angle and beyond. At the point at which an attractive force becomes a repelling force, the first force transmission element 66 moves out of the position shown in FIG. 14 and engages with the second force transmission element 68.

A locking device 74, which can be displaced in the circumferential direction, can be used to fix the position of the first force transmission device 66 relative to the second force transmission device, so that a displacement of one of the two force transmission elements is no longer possible. This prevents the two force transmission elements 66,68 from either engaging or disengaging.

REFERENCE LIST 2 first gearwheel
4 guide rod 6 second gearwheel
8 end face
10 tooth
12 guide spindle
14 end face
16 lateral surface
18 central bore
20 inner wall
22 partial gearwheel(s)
22A second inner partial gearwheel
22B second outer partial gearwheel
23A first inner partial gearwheel
23B first inner partial gearwheel
24 elastic element
26 offset
28 area
30 area
32 spring element
34 elongated hole
36 pin
38 projection
40 magnet
42 upper leg element
44 upper body element
46 pelvic element
50 joint device
52 first splint
54 first swivel axis
56 second splint
58 mechanical energy store
60 first connection element
62 second connection element
64 lever
66 first force transmission element
68 second force transmission element
70 projection
72 openings
74 magnets
76 displacement device
78 magnets
80 positioning magnets
82 counter-magnets

The invention claimed is:

1. An orthopedic device which comprises
a joint with
   a first joint element, comprising a first joint arm, configured to engage a first region of a wearer's body, and mechanically connected to a first positive-locking element, and
   a second joint element, comprising a second joint arm, configured to engage a second region of the wearer's body, a force application lever with a second positive-locking element, and a mechanical energy store, which is arranged between the force application lever and the second joint arm,
wherein:
   the first positive-locking element and the second positive locking element are aligned on a common axis, and are movable toward and away from one another, in an axial direction along the axis, for mutual engagement and disengagement, respectively,
   the first joint element and the second joint element are mutually configured to transfer to a charging and a discharging of the mechanical energy store a swivelling of the first joint arm relative to the second joint arm when the first positive-locking element and the second positive-locking element are in the mutual engagement; and
a safety device for providing, in an engaging of the first positive-locking element to the second positive-locking element, a corrective rotating of the first positive-locking element or the second positive-locking element relative, or both, correcting initial misalignments respective to one another of the first positive-locking element and the second positive-locking element, for improving a security of a force exerted by the charged mechanical energy store being transmitted from the second positive-locking element to the first positive-locking element,
wherein the first positive-locking element and/or the second positive-locking element comprises at least two partial positive-locking elements which are configured as movable independently of each other in the axial direction.

2. The orthopedic device according to claim 1, wherein the safety device is configured to perform the rotating of the first positive-locking element, or the second positive-locking element, or both, relative to one another when the first positive-locking element and the second positive-locking element are engaging with one another.

3. The orthopedic device according to claim 2, wherein:
the first positive-locking element and the second-positive locking element comprise frontal projections and/or recesses, and
the safety device comprises a guide spindle that protrudes in the axial direction, from one among the first positive-locking element and the second positive-locking element, toward the other of the first positive-locking element and the second positive-locking element, and
said guide spindle comprises frontal recesses and/or projections that are configured to engage with the respective other of the first positive-locking element and the second positive-locking element.

4. The orthopedic device according to claim 3, wherein the guide spindle is displaceable in the axial direction relative to the one of the first positive-locking element and the second positive-locking element from which the guide spindle protrudes in the axial direction, the guide spindle being configured in such a way that, upon displacement in the axial direction, the guide spindle is rotated about said axis in a manner wherein a torque is applied to the one among the first positive-locking element and the second positive-locking element that engages with the frontal projections and/or recesses of the guide spindle.

5. The orthopedic device according to claim 2, wherein at least two projections of the first positive-locking elements are configured with an undercut toothing.

6. The orthopedic device according to claim 5, wherein all of the projections of the first positive-locking element and all of the projections of the second positive-locking element are configured with an undercut toothing.

7. The orthopedic device according to claim 1, wherein the at least two partial positive-locking elements comprise the same configuration of projections and/or recesses arranged at an offset from each other in a circumferential direction around the axis.

8. The orthopedic device according to claim 1 5, wherein the at least two partial positive-locking elements are spaced apart from one another in the axial direction when the first positive-locking element and the second positive-locking element are not engaged.

9. The orthopedic device according to claim 1, wherein the first joint element is an upper body element and the second joint element is an upper leg element, and the orthopedic device further comprises a pelvic element, comprising means for urging axial movements of one or both of the first positive-locking element and the second positive-locking element configured for bringing the first positive-locking element and the second positive-locking element into and out of engagement with one another in response to moving the upper body element relative to the pelvic element.

\* \* \* \* \*